(12) United States Patent
Jones et al.

(10) Patent No.: US 11,628,479 B1
(45) Date of Patent: Apr. 18, 2023

(54) AUTOMATED TRACK-BASED CLEANING SYSTEM

(71) Applicants: Anthony Jones, Richardson, TX (US); Ren D. Jones, Garland, TX (US)

(72) Inventors: Anthony Jones, Richardson, TX (US); Ren D. Jones, Garland, TX (US)

( * ) Notice: Subject to any disclaimer, the term of this patent is extended or adjusted under 35 U.S.C. 154(b) by 356 days.

(21) Appl. No.: 16/922,905

(22) Filed: Jul. 7, 2020

(51) Int. Cl.
  *B08B 3/08* (2006.01)
  *B60S 1/64* (2006.01)
  *B08B 13/00* (2006.01)

(52) U.S. Cl.
  CPC ............... *B08B 3/08* (2013.01); *B08B 13/00* (2013.01); *B60S 1/64* (2013.01)

(58) Field of Classification Search
  CPC ........... B08B 3/08; B08B 13/00; B08B 3/024; B08B 2203/02; B60S 1/64; B60S 3/008; B64F 5/30; A61L 2202/25
  See application file for complete search history.

(56) References Cited

U.S. PATENT DOCUMENTS

| | | | |
|---|---|---|---|
| 5,940,927 | A | 8/1999 | Haegermarck et al. |
| 6,481,515 | B1 | 11/2002 | Kirkpatrick et al. |
| 8,506,367 | B2 | 8/2013 | Cermak et al. |
| 8,907,304 | B2 | 12/2014 | Kreitenberg |
| 2006/0124154 | A1* | 6/2006 | Rivalto ............ B08B 3/024 134/103.3 |
| 2009/0193607 | A1 | 8/2009 | Adell et al. |
| 2009/0272409 | A1* | 11/2009 | Petit ............ B60S 3/04 239/548 |
| 2012/0152283 | A1* | 6/2012 | Tiffany ............ B64F 5/30 134/123 |
| 2015/0108244 | A1 | 4/2015 | Pruiett et al. |
| 2018/0201229 | A1* | 7/2018 | Singer ............ B60S 1/522 |
| 2018/0214591 | A1* | 8/2018 | Park ............ B64F 5/30 |

FOREIGN PATENT DOCUMENTS

WO  WO2011076476 A1  6/2011

* cited by examiner

*Primary Examiner* — Michael E Barr
*Assistant Examiner* — Samuel Robert Barker
(74) *Attorney, Agent, or Firm* — Law Office of Sam Sokhansanj PLLC

(57) ABSTRACT

An automated cleaning system is disclosed having a track or rail, and a body having a cylindrical or capsule configuration. The cleaning system further includes a cleaning or disinfectant solution disposed within the body and one or more nozzles secured to one or more sides of the body for dispensing the cleaning solution. The cleaning system also includes one or more wheels or bearings secured to the body, wherein the wheels or bearings are at least partially received within the track. Further, the track can be suspended from overhead within a structure. Here, the cleaning system can be automated and programmed to operate during predefined schedules with little to no human intervention, thereby minimizing the risk associated with cleaning surfaces and open areas, among other advantages.

12 Claims, 10 Drawing Sheets

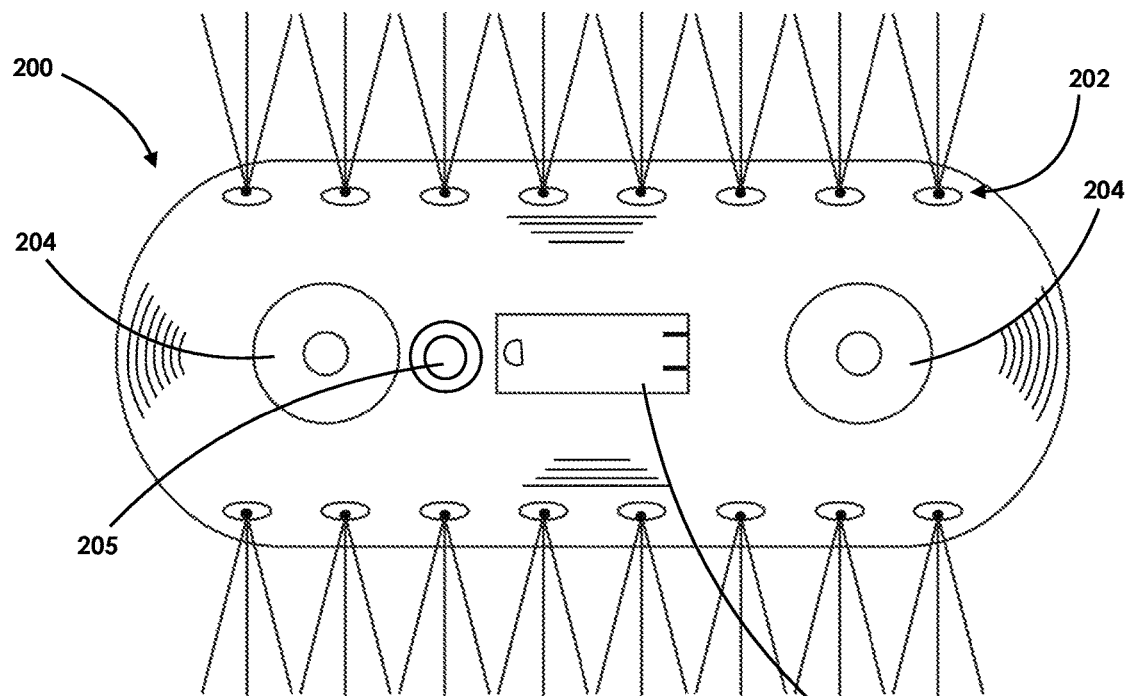
FIG. 3A
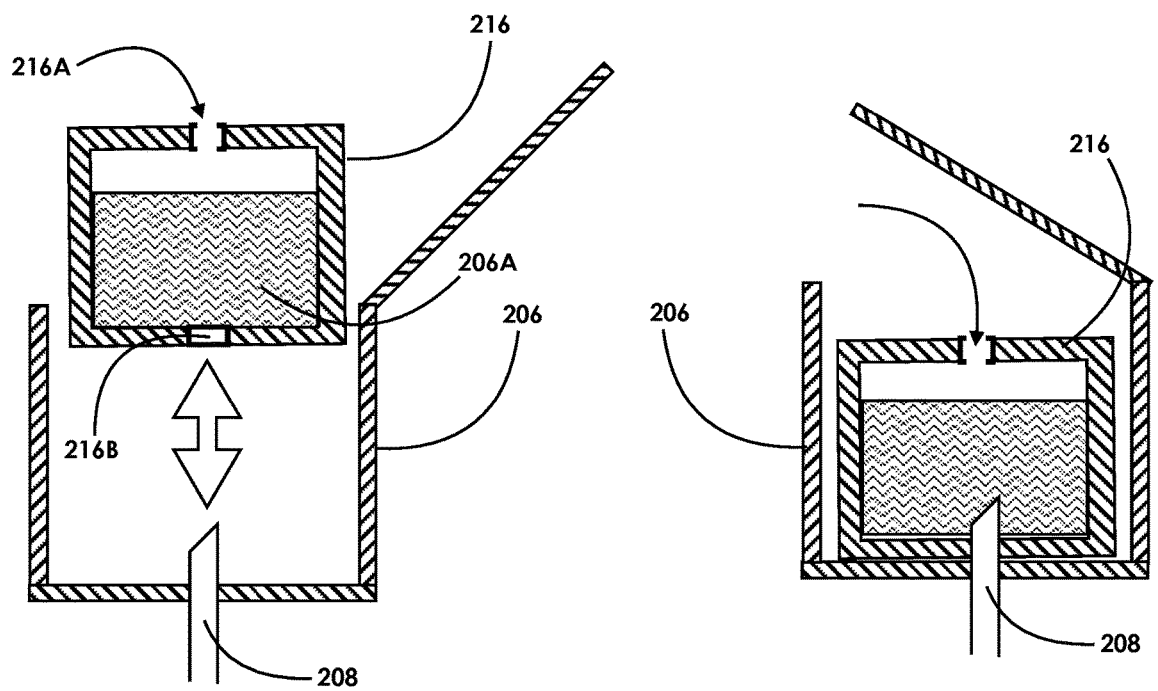
FIG. 3B
FIG. 3C

AUTOMATED TRACK-BASED CLEANING SYSTEM

BACKGROUND

This section is intended to introduce the reader to aspects of art that may be related to various aspects of the present disclosure described herein, which are described and/or claimed below. This discussion is believed to be helpful in providing the reader with background information to facilitate a better understanding of the various aspects of the present disclosure described herein. Accordingly, it should be understood that these statements are to be read in this light, and not as admissions of prior art.

Infectious disease transmission amongst the public is a significant personal and public health concern. Common and potentially serious viral, bacterial, and fungal pathogens are typically spread through the air and from mutually contacted surfaces. Several different types of apparatuses are known for cleaning a surface. One category is, for example, floor cleaning apparatuses that include extraction cleaners for deep cleaning carpets and other fabric surfaces, such as upholstery. However, none of the known devices address cleaning surfaces from the top, overhead, or from a ceiling with an automated system.

Hence, what is needed is an automated system and method of effectively cleaning and disinfecting various surface areas and open areas from an overhead region of a structure, vehicle, or building, among others, with minimal human intervention.

BRIEF SUMMARY

In one aspect of the disclosure described herein, a cleaning system is disclosed having a track or rail, a body having a cylindrical or capsule configuration. The cleaning system further includes a cleaning or disinfectant solution disposed within the body and one or more nozzles secured to one or more sides of the body. The cleaning system also includes one or more wheels or bearings secured to the body, wherein the wheels or bearings are at least partially received within the track. In addition, a compartment is provided wherein the compartment comprises the cleaning solution. Here, the cleaning solution can be disposed within a removable cartridge. Further, the cleaning solution is disposed within an interior cavity of the body. In addition, the cleaning system can include a pump for directing the cleaning solution to the one or more nozzles. Further, the track can have a C-shaped configuration. In addition, the track can be suspended from overhead within a structure. Further, the one or more nozzles can be adjustable. In addition, the track and body can be positioned within a dwelling, structure, vehicle, or aircraft. Here, the cleaning system can be automated and programmed to operate during predefined schedules with little, minimal, or no human intervention, thereby minimizing the risk associated with cleaning surfaces and open areas.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which:

FIG. 3A illustrates a top view of the ATC system and apparatus.

FIGS. 3B-3C illustrate partial cross-sectional side views of a liquid containing compartment of the ATC apparatus.

DETAILED DESCRIPTION

Figure 1:
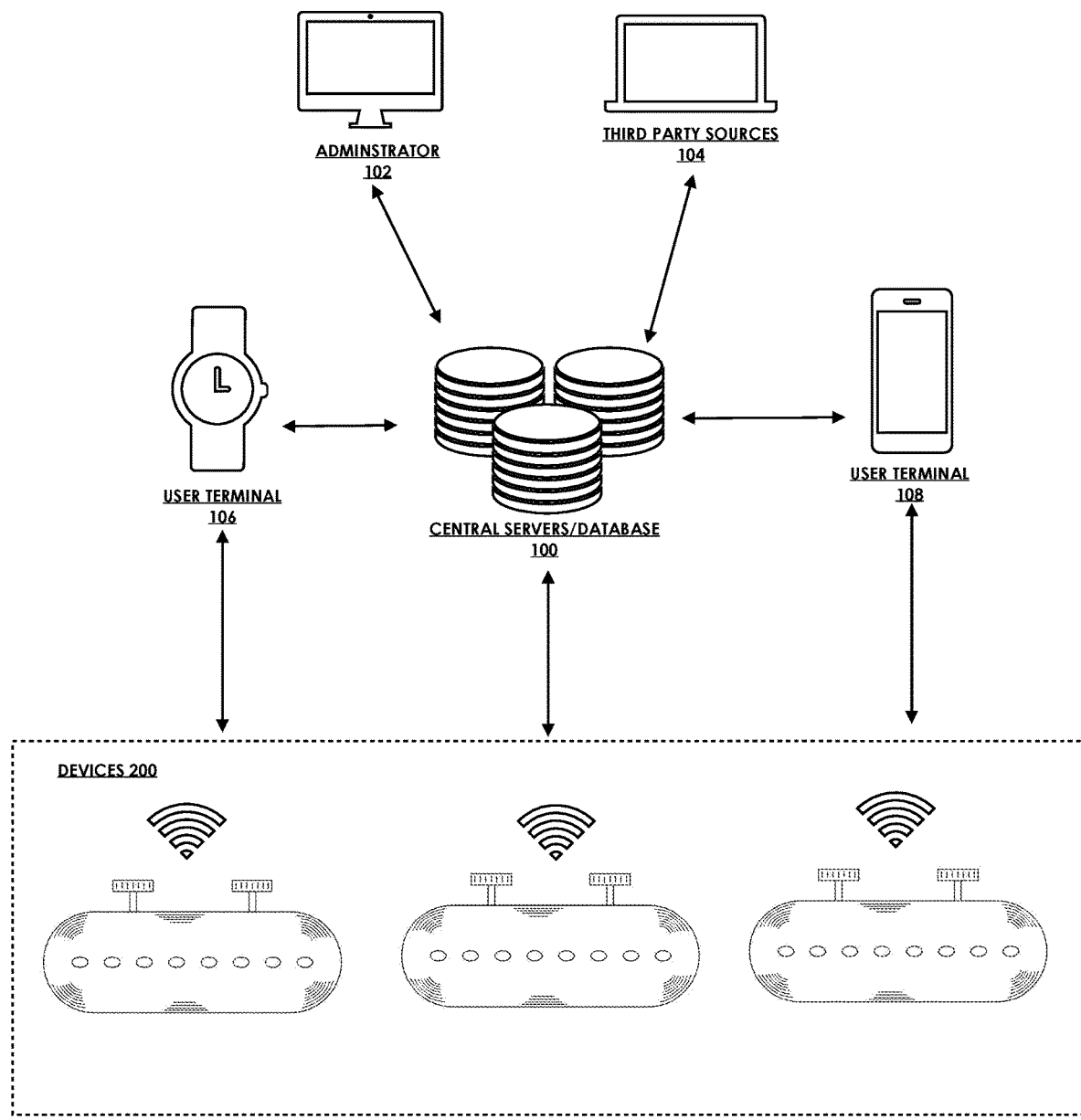
FIG. 1 illustrates an overview block diagram for one non-limiting exemplary embodiment of a network architecture for the automated track-based cleaning (ATC) system and apparatus of the disclosure described herein.

In the Brief Summary of the present disclosure above and in the Detailed Description of the disclosure described herein, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

In one implementation of the disclosure described herein, a display page may include information residing in the computing device's memory, which may be transmitted from the computing device over a network to a central database center and vice versa. The information may be stored in memory at each of the computing devices, a data storage resided at the edge of the network, or on the servers at the central database centers. A computing device or mobile device may receive non-transitory computer readable media, which may contain instructions, logic, data, or code that may be stored in persistent or temporary memory of the mobile device, or may somehow affect or initiate action by a mobile device. Similarly, one or more servers may communicate with one or more mobile devices across a network, and may transmit computer files residing in memory. The network, for example, can include the Internet, wireless communication network, or any other network for connecting one or more mobile devices to one or more servers.

Any discussion of a computing or mobile device may also apply to any type of networked device, including but not limited to mobile devices and phones such as cellular phones (e.g., an iPhone®, Android®, or any "smart phone"), a personal computer, iPad® or other tablet, server computer, or laptop computer; personal digital assistants (PDAs); a roaming device, such as a network-connected roaming device; a wireless device such as a wireless email device or other device capable of communicating wirelessly with a computer network; or any other type of network device that may communicate over a network and handle electronic transactions. Any discussion of any mobile device mentioned may also apply to other devices, such as devices including Bluetooth®, near-field communication (NFC), infrared (IR), and Wi-Fi functionality, among others.

Phrases and terms similar to "software", "application", "app", and "firmware" may include any non-transitory computer readable medium storing thereon a program, which when executed by a computer, causes the computer to perform a method, function, or control operation.

Phrases and terms similar to "network" may include one or more data links that enable the transport of electronic data between computer systems and/or modules. When information is transferred or provided over a network or another communications connection (either hardwired, wireless, or a combination of hardwired or wireless) to a computer, the computer uses that connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Phrases and terms similar to "portal" or "terminal" may include an intranet page, internet page, locally residing software or application, mobile device graphical user interface, or digital presentation for a user. The portal may also be any graphical user interface for accessing various modules, features, options, and/or attributes of the disclosure described herein. For example, the portal can be a web page accessed with a web browser, mobile device application, or any application or software residing on a computing device.

FIG. 1 illustrates one non-limiting exemplary embodiment of a network architecture for the automated track-based cleaning (ATC) apparatus of the disclosure described herein. Here, each ATC device 200 can communicate bi-directionally with a central server or database 100. Specifically, server 100 may send executable instructions to each device 200, wired or wirelessly, that command it to stop or stop cleaning operations, such as cleaning scheduling information. In addition, each device 200 may also send information, wired or wirelessly, to server 100, such as operational data, history data, maintenance data, error data, and the like. Further, each device 200 may also communicate remotely or wirelessly over a network with user devices or terminals 106 and 108. Specifically, a user may manually instruct each ATC device 200 to commence or stop cleaning operations, configure cleaning patterns, cleaning time, cleaning schedule, maintenance, repair, and the like. For example, each user may have a user profile or custom settings associated with each ATC device 200. In addition, the ATC device 200 may have a dedicated stand-alone "app," application, or software for operating it via a user mobile device. Further, each ATC device 200 or servers 100 may communicate with an administrator terminal, wherein an administrator can provide various use privileges to other users. In addition, the administrator can also remotely manage and operate each device 200. Further, each ATC device 200 or servers 100 may also communicate with a third party source 104, such as retrieving third party data or transmitting data to third parties, such as tracking/history information.

Figure 2:
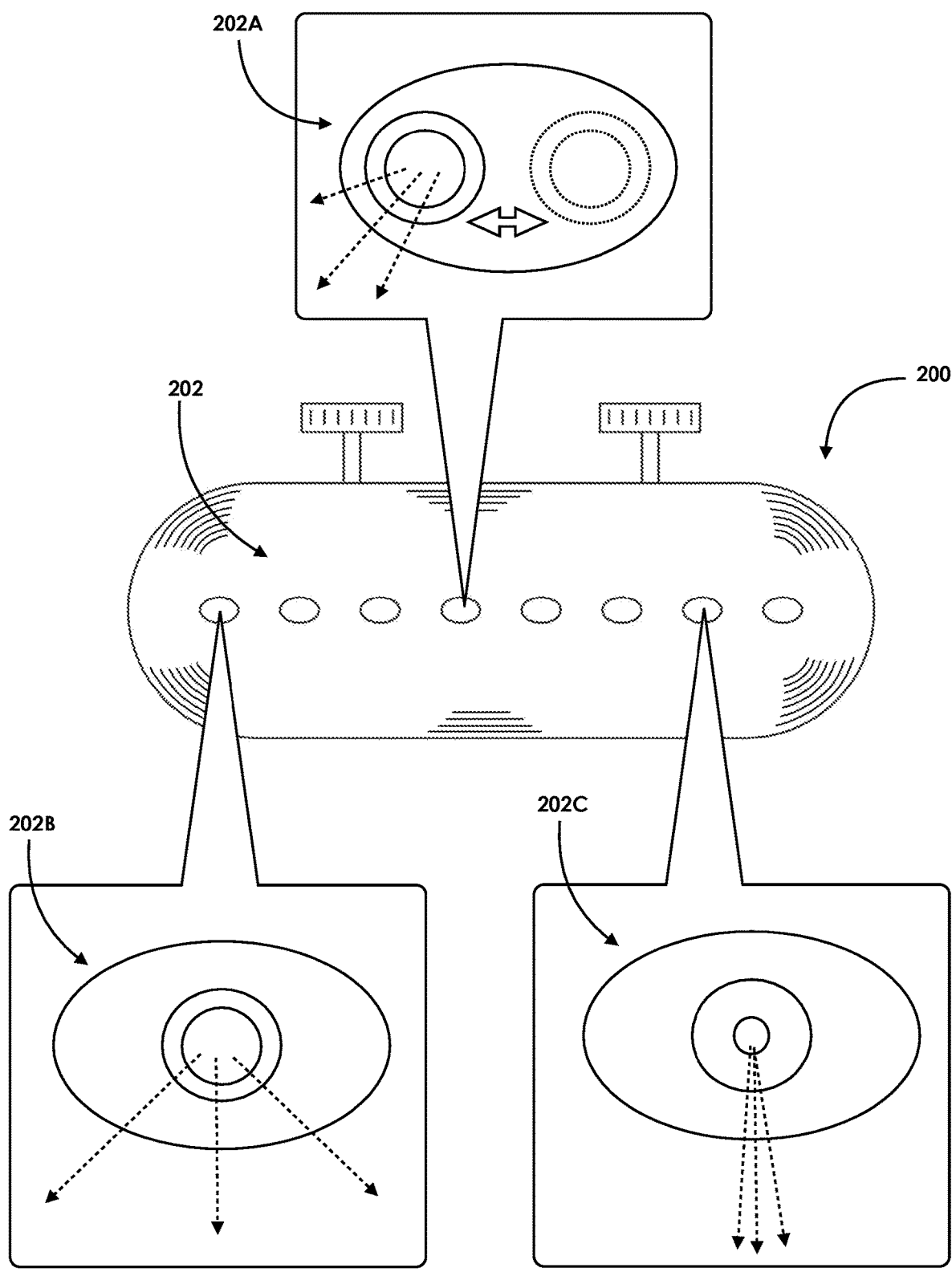
FIG. 2 illustrates a side view of the automated track-based cleaning (ATC) apparatus and close-up front views of various non-limiting embodiments of nozzle configurations of the ATC system and apparatus.

FIG. 2 illustrates a side view of the ATC device 200 having a body or casing in a cylindrical or capsule type configuration. ATC device 200 further includes multiple nozzles 202 arranged in a horizontal configuration along the body of ATC device 200. Here, a nozzle 202A may have adjustment members that allow it to pivot from left to right or up or down (manually or motorized/automated) to provide a liquid spray pattern. Nozzle 202B may be adjustable to provide a wide-angle spray pattern (manually or motorized/automated). Nozzle 202C may also be adjustable to provide a narrow spray pattern (manually or motorized/automated).

Figure 4A:
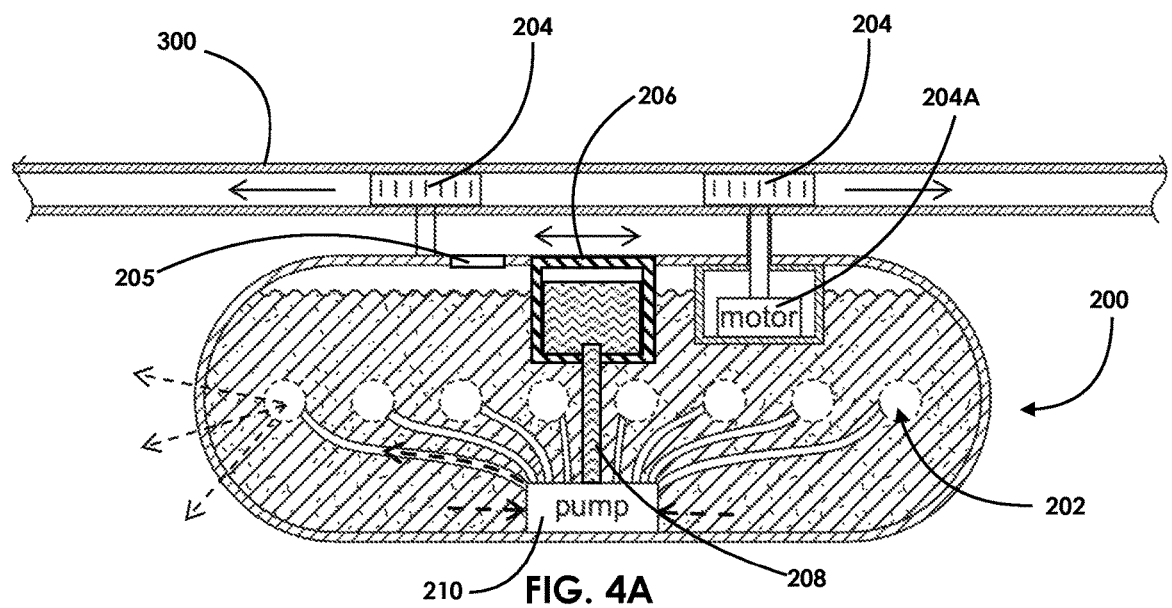
FIG. 4A illustrates a partial cross-sectional side view of the ATC system and apparatus secured to a track.
Figure 4B:
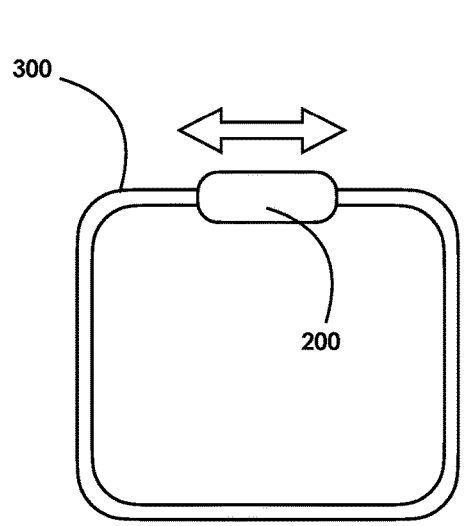
FIG. 4B illustrates a simplified bottom view for one non-limiting exemplary embodiment of a track configuration for the ATC system and apparatus.
Figure 4C:
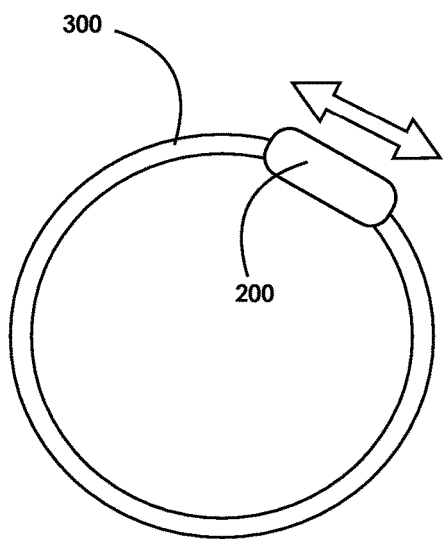
FIG. 4C illustrates a simplified bottom view for another non-limiting exemplary embodiment of a track configuration for the ATC system and apparatus.

FIGS. 3A-4A illustrate various views of the ATC apparatus of the disclosure described herein. Here, ATC device 200 is further shown having a set of wheels or bearings 204, as also shown in FIG. 4A. Here, wheels 204 are adapted to slide or roll within an overhead fixed rail or track 300. In addition, either or both of wheels 204 may have a motor 204A and drive shaft and gears connected to the wheel for driving device 200 forward or backwards along the track via the wheels 204, as shown in FIG. 4A. FIG. 3A also shows a fluid or liquid cleaning compartment 206 having a closable and sealable lid for access and removal of a cleaning cartridge 216. As shown in FIGS. 3B-3C, compartment 206 can include a cleaning fluid cartridge 216 having a cleaning fluid, such as a concentrated liquid cleaning or disinfectant solution/composition/formulation 206A therein. In addition, cartridge 206 may be disposable (removed and replaced) or it may be refilled with additional fluid 206A via a port or inlet 216A. In addition, cartridge 206 may include a lower outlet or port 216B having a puncturable seal that allows it to dispose of its contents via tube or piping 208 of ATC device 200 to pump 210 or interior region of device 200.

Still referring to FIGS. 3A-4A, device ATC device 200 may also include a separate inlet port 205 that allows a user to insert additional fluids inside of ATC device 200. Specifically, the interior body of ATC device 200 may operate as a reservoir that can be filled with additional cleaning/disinfectant solution (or backup cleaning/disinfectant solution), or in the alternative, it may be used to fill ATC device 200 with water that can then be mixed with solution 206A at pump 210 to be dispensed via nozzles 202. Specifically, pump 210 can operate to draw fluids from either, or both, of the interior body of device 200 and/or from compartment 206 to be dispensed via additional tubing connected to each of nozzles 202. Alternatively, a mixer or agitator component may be included before or after the pump for mixing/agitating the filled water with cleaning solution. Here, FIGS. 4B-4C further illustrate various embodiments of a configuration for tracks 300, having a square or round like pattern.

Figures 5, 5A, 5B:
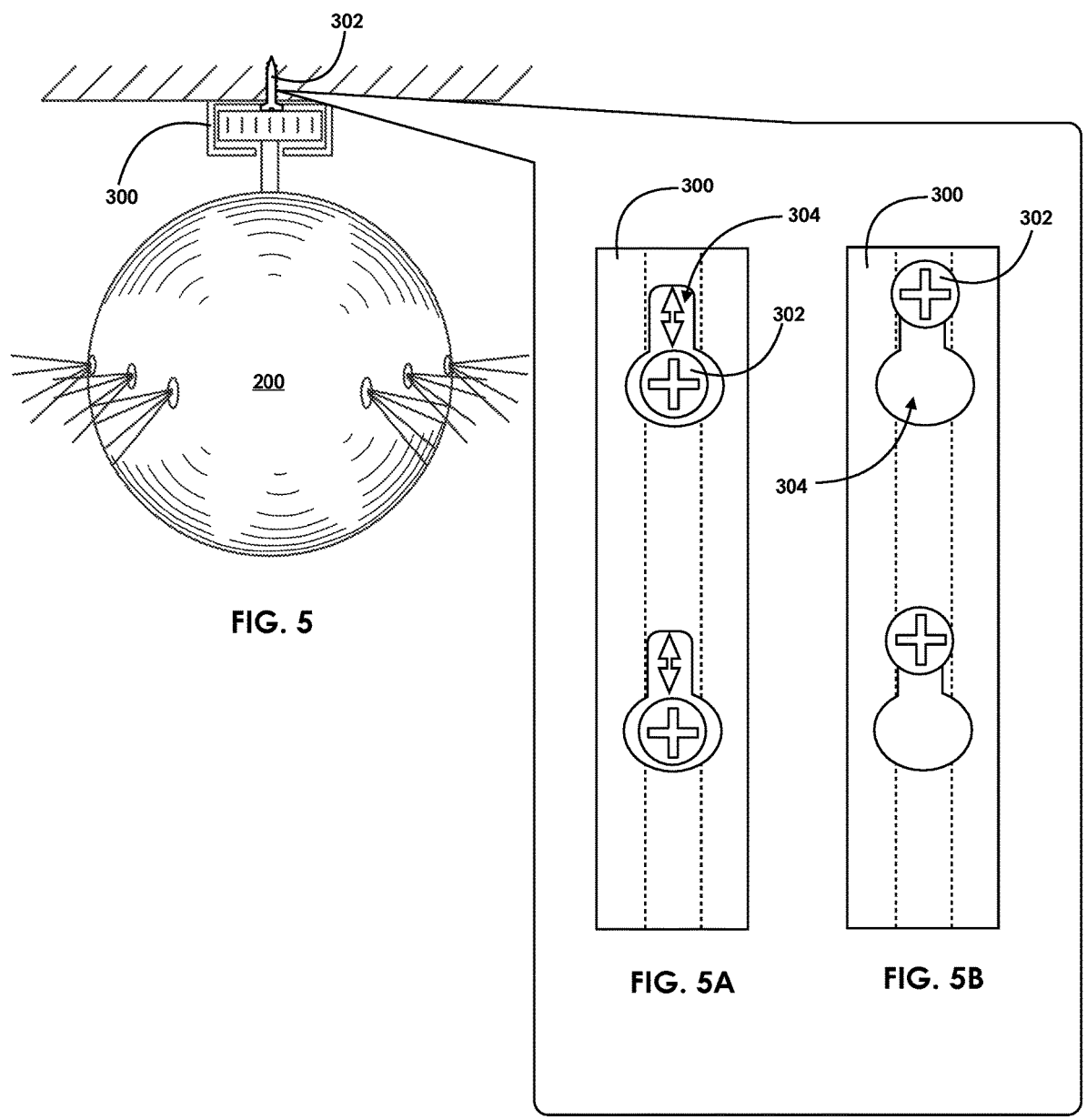
FIG. 5 illustrates a front view of the ATC system and apparatus and track securement members.
FIGS. 5A-5B illustrates a bottom view of the track and track securement members for the ATC apparatus of the disclosure described herein.

FIGS. 5-5B illustrates one non-limiting exemplary embodiment of a method of securing track 300 to an overhead roof, ceiling, or structure. Specifically, track 300 may be provided at any length and across any distance. In addition, track 300 may be provided in separate pieces connected (or interlocked) to each other in series to extend to any length. In addition, track 300 may be configured in an inverted C-shaped configuration wherein the opening of the track allows a shaft connecting the wheels 204 to the body of ATC device 200 to move freely along the track, while wheels 204 are partially enclosed with track 300 and guide and/or drive the body of ATC device 200 along the interior wall regions of track 300. Here, track 300 may have key-type slots 304 along its length that allow a securement member, such as a screw or bolt, to slide within it and the securement member then further secured or drilled into place thereby firmly holding and affixing track 300 to the structure.

Figure 6A:
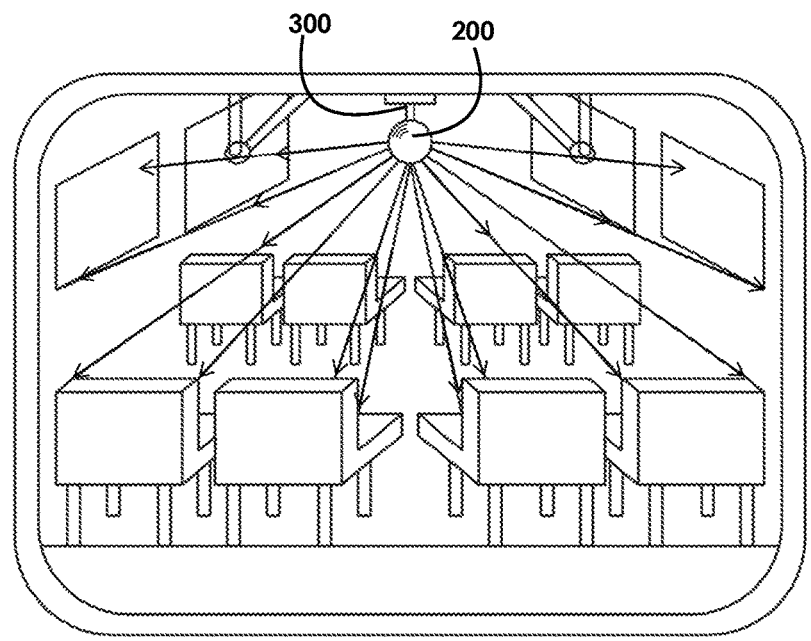
FIG. 6A illustrates a perspective view for one non-limiting exemplary embodiment of an interior of a movie theater having the ATC apparatus and track system.
Figure 6B:
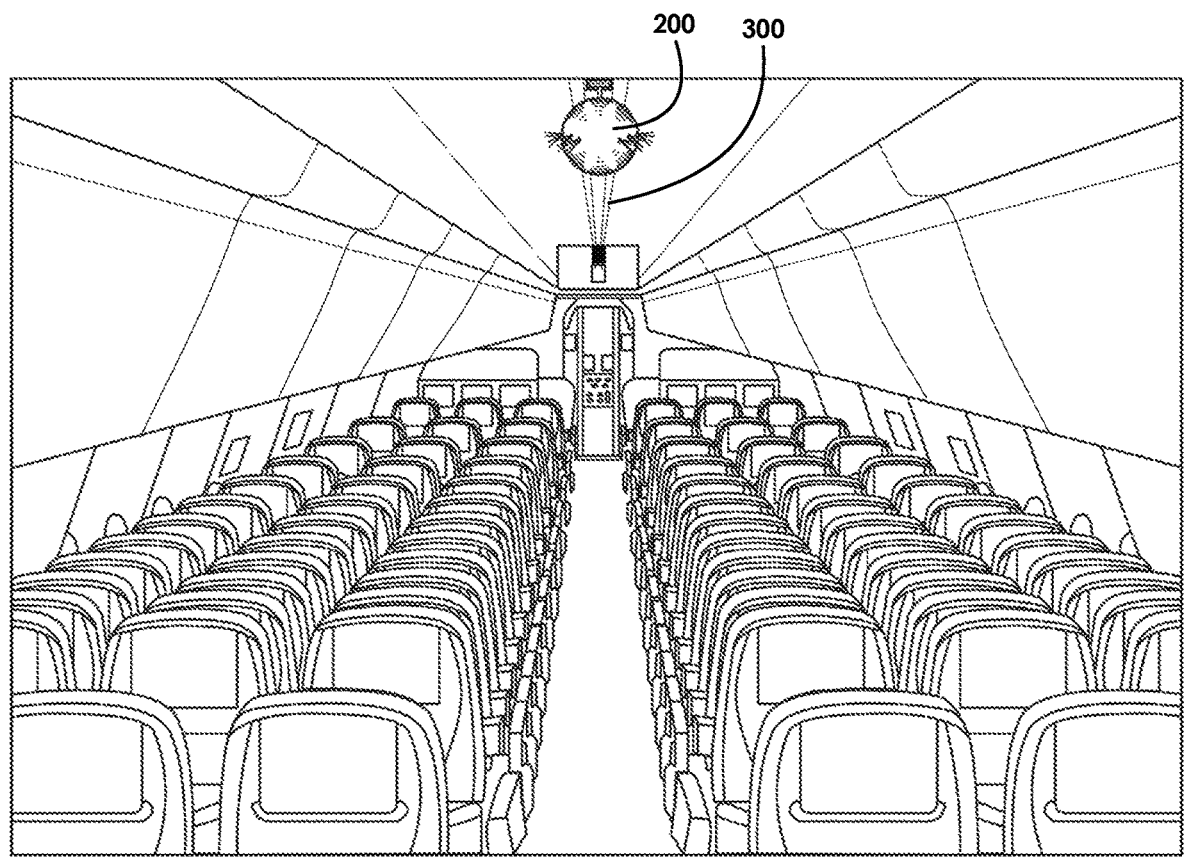
FIG. 6B illustrates a perspective view for one non-limiting exemplary embodiment of an airplane cabin having the ATC apparatus and track system.

FIGS. 6A-6D illustrate various methods, environments, and configurations for operating ATC device 200 and its associated track 300. For example, as shown in FIG. 6A, ATC device 200 and track 300 may be configured within a movie theater, such that track 300 is secured to the ceiling of the theater and ATC device 200 operates to dispense cleaning solution from overhead and onto the seats, floor, and railings of the movie theater. In another example, as shown in FIG. 6B, ATC device 200 and track 300 may be configured within a cabin of an aircraft, such that track 300 is secured to the ceiling/overhead region of the cabin and ATC device 200 operates to dispense cleaning solution from overhead and onto the aircraft seats, tray tables, windows, floor, and railings of the aircraft from within. In this example, ATC device 200 may be operated during cleaning operations within the cabin of the aircraft, such as between flights, wherein ATC device 200 can move up and down the cabin area repeatedly for a specified time in order to thoroughly disinfect the interior of the aircraft cabin (such as from first class area to coach area).

Figure 6C:
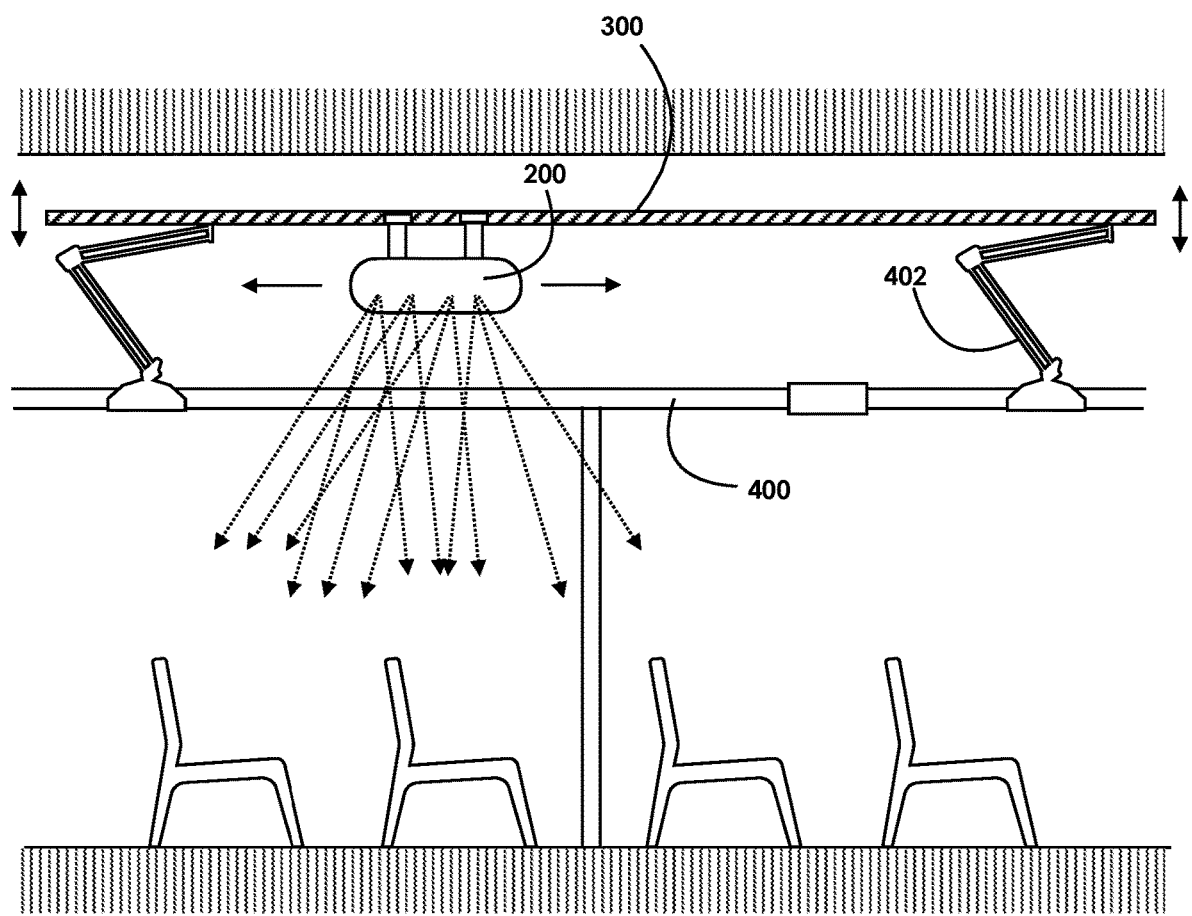
FIG. 6C illustrates a side view for one non-limiting exemplary embodiment of a passenger vehicle or bus interior having the ATC apparatus and another non-limiting embodiment of a track system.
Figure 6D:
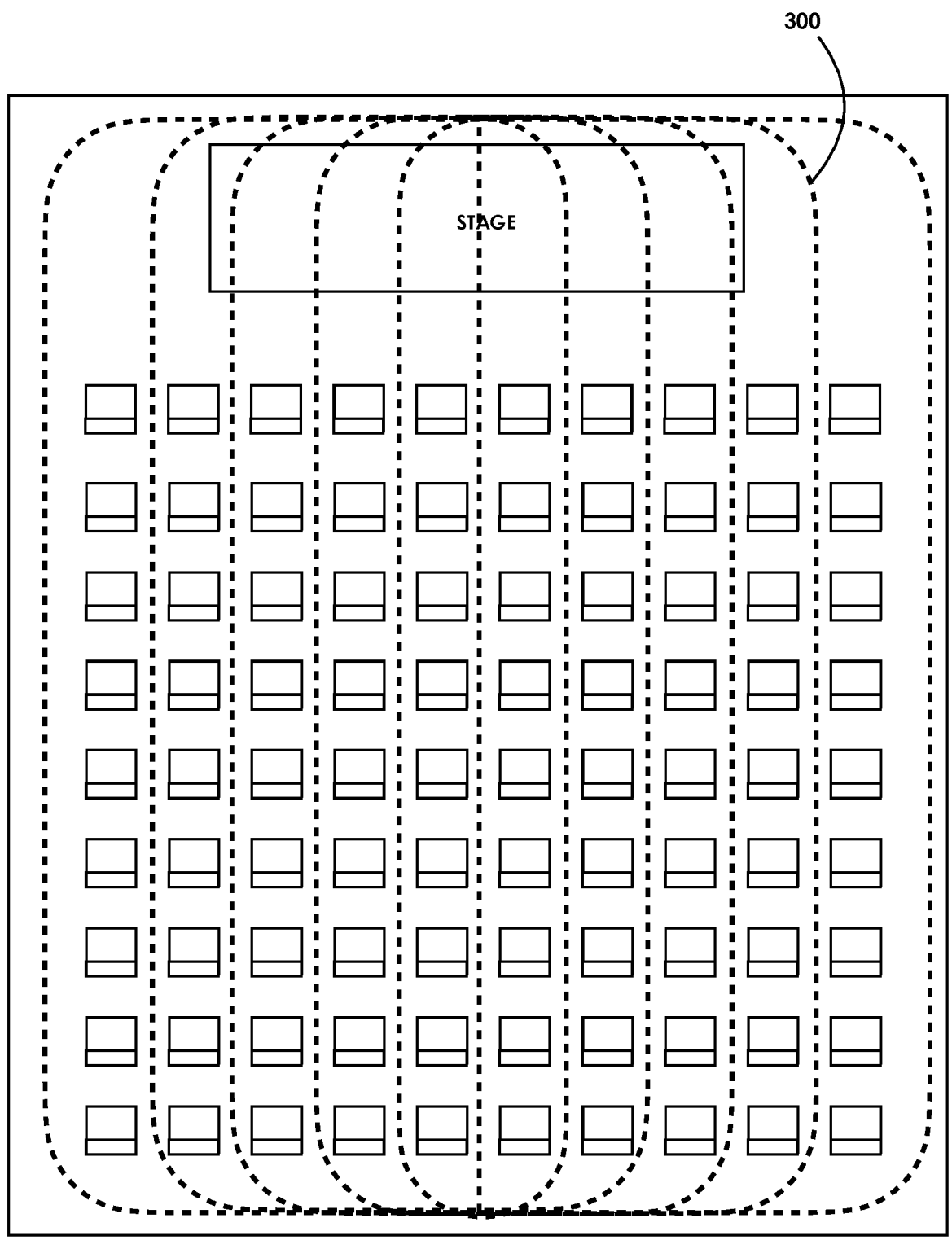
FIG. 6D illustrates a top view for one non-limiting exemplary embodiment of an auditorium having the ATC apparatus and another non-limiting exemplary embodiment of a configuration for the track system.
Figures 7A, 7B:
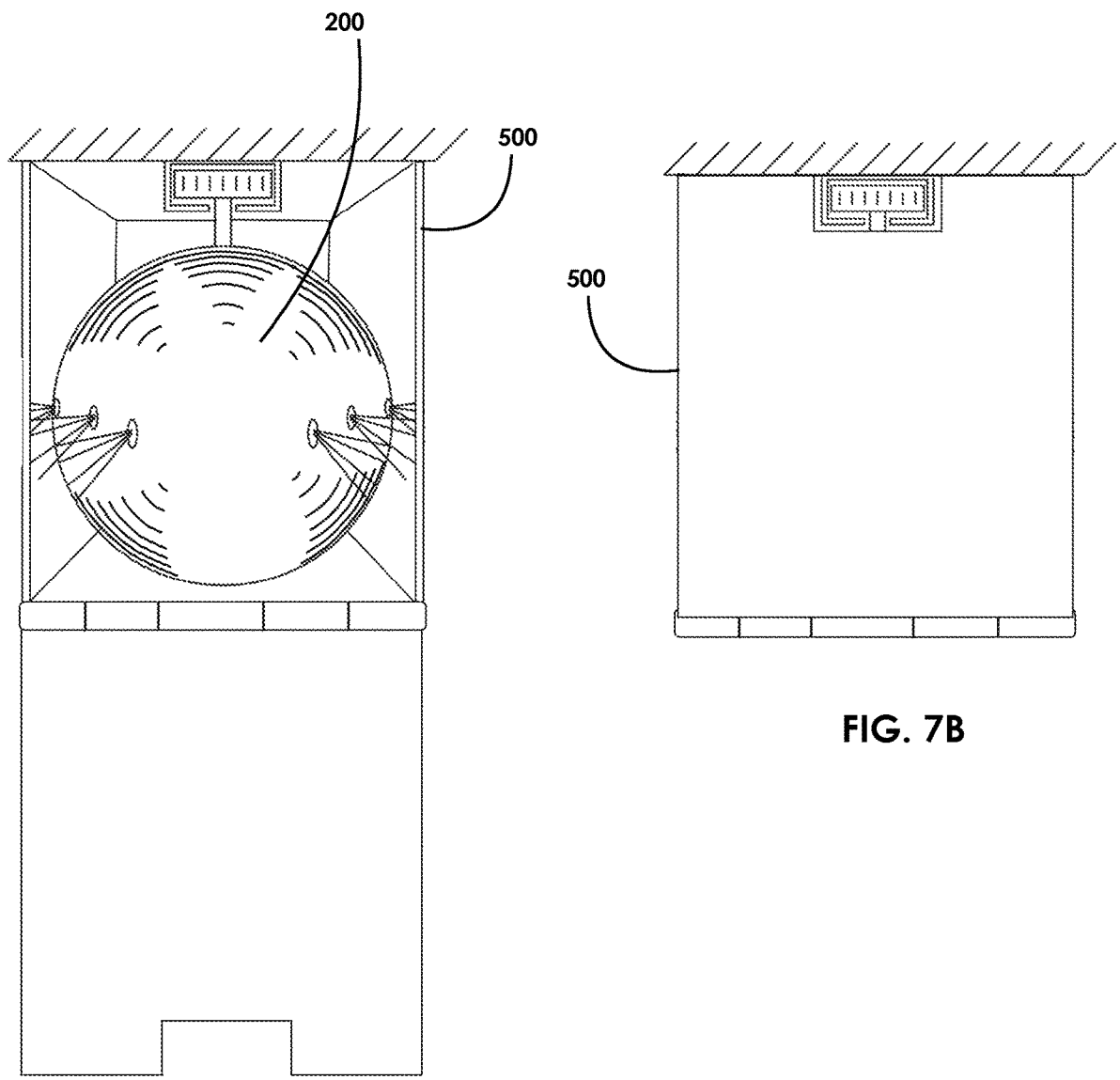
FIGS. 7A-7B illustrates a perspective front view for one non-limiting exemplary embodiment of an enclosure or storage compartment for the ATC system and apparatus.
Figure 8A:
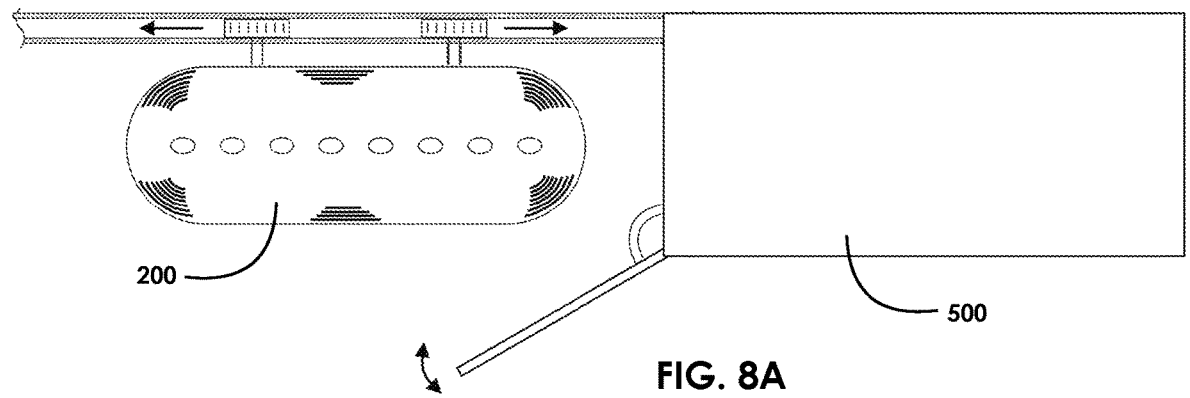
FIGS. 8A-8C illustrates a side view for the enclosure or storage compartment of FIGS. 7A-7B.
Figure 8B:
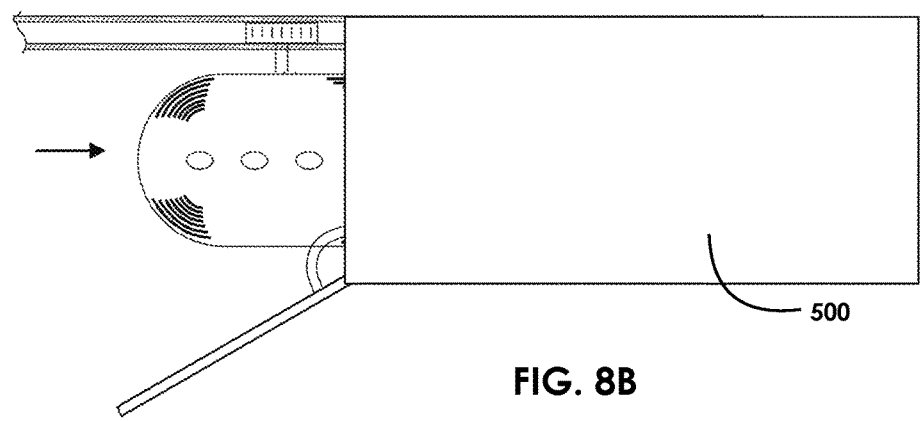
Figure 8C:
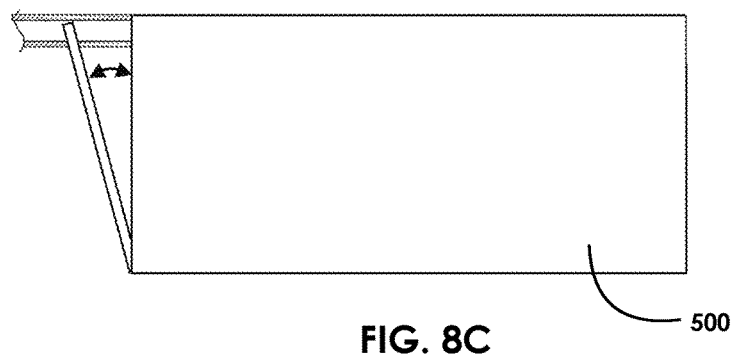

In another example, as shown in FIG. 6C, ATC device 200 and track 300 may be configured within a passenger bus vehicle. Here, in lieu of being secured to the ceiling of the vehicle, track 300 may be secured and placed overhead via railings 400 within the vehicle. Specifically, an adjustable height articulating arm or separate bracket 402 may have one end secured to railing 400 and another end secured to track 300. In this example, track 300 can then be suspended from overhead, wherein ATC device 200 can move laterally within the interior of the passenger bus thereby spraying and cleaning the interior cabin, such as the seats, railings, floor, windows, and the like. FIG. 6D illustrates another example of a configuration pattern for track 300 of ATC device 200. In this example, track 300 may be continuous (or have switchable rail tracks) that allow ATC device to operate along each row of seats within an auditorium in a looping pattern, such as via one ATC device 200 or multiple ATC devices 200.

FIGS. 7A-8C illustrate a storage unit for ATC device 200. Specifically, storage unit 500 includes a manually or automatically (motor driven) hinged lid or cover that encloses ATC device 200 within. In addition, storage unit 500 may also include additional functionality, such as having the ability to charge one or more battery components of ATC device 200 (such as via wireless charging), refill one or more cartridges or interior body of ATC device 200 with water or cleaning solution, and/or communicate with other computing devices by interfacing with one or more data communication ports within storage unit 500, among others.

From the foregoing it will be seen that the present disclosure described herein is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts described herein, except insofar as such limitations are included in following claims. Further, it will be understood that certain features and sub-combinations are of utility and may be employed without reference to other features and sub-combinations. This is contemplated by and is within the scope of the claims.

What is claimed is:

1. A cleaning system, comprising:
   an overhead track;
   a body having a capsule configuration;
   a cleaning solution disposed within the body;
   a plurality of independently pivoting nozzles secured to opposing sides of the body;
   at least one wheel disposed above the body and coupled to the body via a drive shaft, wherein the at least one wheel is at least partially received within the track; and
   a motor disposed within the body, wherein the motor is coupled to the drive shaft and configured to operate the at least one wheel.

2. The cleaning system of claim 1, further comprising a compartment.

3. The cleaning system of claim 2, wherein the compartment comprises the cleaning solution.

4. The cleaning system of claim 3, wherein the cleaning solution is disposed within a removable cartridge.

5. The cleaning system of claim 1, wherein the cleaning solution is disposed within an interior cavity of the body.

6. The cleaning system of claim 1, further comprising a pump for directing the cleaning solution to the plurality of nozzles.

7. The cleaning system of claim 1, wherein the track is comprised of a C-shaped configuration.

8. The cleaning system of claim 1, wherein the track is suspended from a structure.

9. The cleaning system of claim 1, wherein the plurality of nozzles comprise adjustable spray patterns.

10. The cleaning system of claim 1, wherein the track and body are positioned within a dwelling, structure, vehicle, or aircraft.

11. A cleaning system, comprising:

a track;

a body having a capsule configuration;

a plurality of independently pivoting nozzles secured to opposing sides of the body;

at least one wheel disposed above the body and coupled to the body via a drive shaft, wherein the at least one wheel is at least partially received within the track; and a motor coupled to the drive shaft and configured to operate the at least one wheel.

12. A cleaning system, comprising:

a track;

a body having a capsule configuration;

a plurality of nozzles secured to opposing sides of the body adapted to dispense a cleaning solution;

at least one wheel disposed above the body and coupled to the body, wherein the at least one wheel is at least partially received within the track; and a motor coupled to the drive shaft and configured to operate the at least one wheel.

\* \* \* \* \*